United States Patent [19]

Young

[11] 4,301,316
[45] Nov. 17, 1981

[54] PREPARING PHENYLALKANES

[75] Inventor: Lewis B. Young, Skillman, N.J.

[73] Assignee: Mobil Oil Corporation, New York, N.Y.

[21] Appl. No.: 96,094

[22] Filed: Nov. 20, 1979

[51] Int. Cl.³ .......................... C07C 2/64; C07C 15/07
[52] U.S. Cl. ..................................... 585/455; 585/467
[58] Field of Search ................................ 585/455, 467

[56] References Cited

U.S. PATENT DOCUMENTS

| | | | |
|---|---|---|---|
| 3,716,596 | 2/1973 | Bowes | 585/455 |
| 3,972,983 | 8/1976 | Ciric | 423/328 |
| 4,049,738 | 9/1977 | Young | 260/671 M |
| 4,049,739 | 9/1977 | Zabransky et al. | 585/467 |
| 4,070,407 | 1/1978 | Haag et al. | 260/671 R |
| 4,100,215 | 7/1978 | Chen | 585/467 |
| 4,100,217 | 7/1978 | Young | 260/671 R |
| 4,136,128 | 1/1979 | Haag et al. | 260/671 R |
| 4,157,950 | 6/1979 | Frilette et al. | 585/467 |

FOREIGN PATENT DOCUMENTS 1069242  5/1967  United Kingdom.

*Primary Examiner*—Curtis R. Davis
*Attorney, Agent, or Firm*—Charles A. Huggett; Ronald J. Cier; George W. Allen

[57] ABSTRACT

A process for the selective alkylation of substituted or unsubstituted benzene compounds with relatively long chain length alkylating agents to produce phenylalkanes having an improved yield of the more external phenyl isomers. The reaction is carried out in the presence of crystalline zeolite catalysts, such as ZSM-4, ZSM-20, ZSM-38, mazzite, Linde Type L and zeolite Beta.

11 Claims, No Drawings

PREPARING PHENYLALKANES

BACKGROUND OF THE INVENTION

1. Field of the Invention

This invention is concerned with alkylation of aromatic compounds and, in particular, it is directed to a method for production of relatively long chain length phenylalkanes.

2. Description of the Prior Art

Conventional Friedel-Crafts alkylations of aromatic compounds with linear olefins, carried out in the presence of $AlCl_3$ or other Lewis acid as catalyst, are known to produce linear secondary phenylalkanes which are typically a mixture of all of the conceivable positional isomers—i.e. 2-phenyl, 3-phenyl, 4-phenyl, etc. Primary phenylalkanes and products with side chain branching are not usually formed. For example, the reaction of benzene and 1-dodecene in the presence of $AlCl_3$ gives a product mix as follows:

| Benzene + 1-$C_{12}$ = $\xrightarrow{AlCl_3}$ #-Phenyldodecane | |
|---|---|
| Position of Phenyl Substituent, # | Composition |
| 1 | 0% |
| 2 | 30% |
| 3 | 19% |
| 4 | 17% |
| 5 | 17% |
| 6 | 17% |

The composition of the phenyldodecane mixture is somewhat dependent upon the acid catalyst involved. For instance, $H_2SO_4$ catalyst has been reported to result in 41% 2-phenyldodecane while HF yields 20% 2-phenyldodecane in the phenyldodecane product mix. Similar results can be shown for other alkylations involving relatively large (i.e. >$C_5$) alkylating agents.

Commercial production of linear alkylbenzenes by the Friedel-Crafts route presently exceeds 500 million pounds per year. The vast majority of this production is subsequently sulfonated to produce alkylbenzene sulfonic acids for the detergent industry. Other known routes for alkylation of benzenes with long chain alkylating agents include utilization of acidic ion exchange resins and of faujasites. Highly acidic faujasites such as REY and REX have been shown to be potentially useful by the work of P. B. Venuto et al published in the JOURNAL OF CATALYSIS, 4, 81–98 (1966).

SUMMARY OF THE INVENTION

Certain crystalline zeolites have now been found to promote the reaction of aromatic compounds with relatively long chain-length alkylating agents to give an unexpectedly high yield of linear phenylalkanes. These zeolites also demonstrated a surprising tendency to produce isomeric phenylalkane product mixtures in which the proportion of phenyl substitution on the relatively more external carbon atoms of the alkyl group (e.g. the #2-carbon) was significantly higher than that previously encountered.

The process is carried out by bringing the aromatic compound, which may be a substituted or unsubstituted benzene, into contact with the alkylating agent in the presence of the crystalline zeolite catalyst. The reaction is conducted at conditions of temperature and pressure suitable for promoting such alkylation reaction, preferably between about 50° C. and 500° C. and at pressures within the approximate range of $2.5 \times 10^4$ $N/m^2$ through $2.5 \times 10^7$ $N/m^2$ (0.25–250 atmospheres). Crystalline zeolites found useful herein include those materials known in the art as: mazzite, Linde Type L, zeolite Beta, ZSM-4, ZSM-20 and ZSM-38, and including synthetic and naturally occurring isotypes thereof.

DESCRIPTION OF SPECIFIC EMBODIMENTS

It is contemplated that alkylating agents useful in the process of this invention will include any aliphatic or aromatic organic compound, having one or more available alkyl groups of at least five carbon atoms, which are capable of reacting with an aromatic compound. Useful alkylating agents include, for example, alkyl halides, olefins or alcohols having a linear hydrocarbon chain length or "backbone" of at least five (5) carbon atoms, and preferably from about 6 to about 20 carbon atoms. Olefins are the preferred alkylating agents, although one may plainly substitute any other hydrocarbon material which will generate unsaturated carbon atoms in the presence of the disclosed alkylation catalysts.

The aromatic compounds which are to be reacted with the foregoing alkylating agents to yield the desired phenylalkanes by the process disclosed herein are benzene compounds. These benzene compounds may be unsubstituted, or they may carry from 1 to 2 substituents on the ring structure. If substituted, the substituent may be an alkyl group having from 1 to 10 carbon atoms therein, or may be a halide, an alkoxy, an aryl group, hydroxy, acid and so forth, or any combination of these or other substituents.

The zeolites utilized in the process of this invention may be either naturally occurring or synthetic crystalline zeolites. Preferred materials are mazzite, Linde Type L, zeolite Beta, ZSM-4, ZSM-20 and ZSM-38, and including synthetic and naturally occurring isotypes thereof, such as zeolite Omega, zeolites Ba-G, K-G, P-L, and others.

ZSM-4 and methods for producing this material are described in U.S. Pat. No. 3,923,639. This patent, and in particular the portion thereof setting forth the characteristic X-ray diffraction pattern of ZSM-4, is incorporated herein by reference.

ZSM-20 and methods for the production thereof are described in U.S. Pat. No. 3,972,983. This patent, and in particular the portion thereof setting forth the characteristic X-ray diffraction pattern of ZSM-20, is incorporated by reference.

ZSM-38 is described in U.S. Pat. No. 4,046,859, as are methods useful for producing this material. Such patent, and especially the disclosure therein relating to the characterizing X-ray diffraction pattern of ZSM-38, is likewise incorporated herein by reference.

Characterizing data pertaining to zeolite Beta, including methods for synthesizing this material, are disclosed in U.S. Pat. No. 3,308,069. The contents of this issued patent, and in particular the characteristic X-ray diffraction pattern of zeolite Beta, are incorporated herein by reference.

Linde Type L zeolite and methods for producing such material are to be found in U.S. Pat. No. 3,216,789. The entire contents of this patent, particularly the portion thereof relating to the characteristic X-ray diffraction pattern of the Type L zeolite, are also incorporated herein by reference.

The zeolites useful in the conversion process of this invention generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen precursors, e.g. ammonium ions, which upon calcination yield the hydrogen form. This exchange is conveniently carried out by contact of the zeolite with an ammonium salt solution, e.g. ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

An especially useful modifying treatment entails steaming of the zeolite by contact with an atmosphere containing from about 5 to about 100 percent steam at a temperature of from about 250° to 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

In practicing the desired conversion process, it may be desirable to incorporate the above-described crystalline zeolites in another material resistant to the temperature and other conditions employed in the process. Such matrix materials include synthetic or naturally occurring substances as well as inorganic materials such as clay, silica, and/or metal oxides. The latter may be either naturally occurring or in the form of gels or gelatinous precipitates including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment, or chemical modification.

In addition to the foregoing materials, the zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia, and silica-magnesia-zirconia. The matrix may be in the form of a cogel. The relative proportions of finely divided zeolite and inorganic oxide gel matrix may vary widely, with the zeolite content ranging from between about 1 to about 99 percent by weight and more usually in the range of about 5 to about 80 percent by weight of the composite.

The process of this invention is conducted such that the organic reactants, i.e. the aromatic compound and the alkylating agent, are brought into contact with the zeolite in a suitable reaction zone, such as for example in a flow reactor containing a fixed bed of the catalyst, under effective alkylation conditions. Such conditions include a temperature of between about 50° C. and about 500° C., a pressure of between about $2.5 \times 10^4$ $N/m^2$ and about $2.5 \times 10^7$ $N/m^2$ (0.25–250 atmospheres), and a feed weight hourly space velocity (WHSV) of between about 0.1 and about 500. The latter WHSV is based upon the weight of the catalyst compositions employed, i.e. the total weight of active catalyst and binder therefor. Preferred reaction conditions include a temperature within the approximate range of 100° C. to 350° C. with a feed WHSV of between 0.5 and 100. Although the reaction normally takes place at atmospheric pressure ($10^5$ $N/m^2$), the preferred pressure range extends from about $10^5$ $N/m^2$ to about $5 \times 10^6$ $N/m^2$. The reactants may be in either the vapor phase or the liquid phase and may be neat, i.e. free from intentional admixture or dilution with other material, or may be brought into contact with the zeolite with the aid of carrier gases or diluents such as, for example, hydrogen or nitrogen.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The following examples are provided to illustrate the process of this invention and aid those in the art in the understanding thereof, but clearly should not be taken as presenting undue limitations thereon:

EXAMPLE 1

(ZSM-4)

Benzene and 1-dodecene were reacted, at a molar ratio of 4:1, in the presence of the zeolite HZSM-4. The organic reactants were passed over the catalyst in a flow reactor at a WHSV of 30 $hr^{-1}$. Reactor temperature was 205° C. and the pressure was maintained at 210 psig. Analysis of the reactor effluent showed that the 1-dodecene conversion level was 92% with 73% selectivity to phenyldodecane product. Isomeric distribution was as follows: 57% 2-phenyldodecane, 25% 3-phenyldodecane, 8% 4-phenyldodecane, 5% 5-phenyldodecane and 5% 6-phenyldodecane, with 90% of the phenyldodecane product being linear.

EXAMPLE 2

(Beta)

Zeolite Beta ($SiO_2/Al_2O_3 = 175$) was placed in a flow reactor at 250° C. and 600 psig. A feed stream consisting of benzene and 1-dodecene (molar ratio=4:1) was passed over the catalyst at WHSV of 30 $hr^{-1}$. Analysis of the product stream indicated a 38% conversion of $C_{12}=$ with 47% selectivity to phenyldodecane. Isomeric phenyldodecanes were: 57% 2-phenyldodecane, 18% 3-phenyldodecane, 10% 4-phenyldodecane, 7%

5-phenyldodecane and 8% 6-phenyldodecane, with 53% selectivity to the linear product.

EXAMPLE 3

(ZSM-20)

Utilizing the same reaction conditions and feed stream as Example 2, benzene and 1-dodecene were brought into contact with ZSM-20 zeolite. Conversion of dodecene was 26% and selectivity to phenyldodecane 33%. Isomeric distribution of phenyldodecanes in the product was: 51% 2-phenyldodecane, 21% 3-phenyldodecane, 11% 4-phenyldodecane, 9% 5-phenyldodecane and 8% 6-phenyldodecane. Substantially the entire phenyldodecane product was linear.

EXAMPLE 4

(Linde Type L)

Linde Type L zeolite was placed in the flow reactor and the benzene/1-dodecene feed stream (4:1 molar ratio) passed across the catalyst at 195° C. and 210 psig with WHSV of 30 hr$^{-1}$. Dodecene conversion rate was 72% and selectivity to phenyldodecane also 72%. The phenyldodecane product, 88% of which was linear, was composed of 40% 2-phenyldodecane, 18% 3-phenyldodecane, 16% 4-phenyldodecane, 15% 5-phenyldodecane and 11% 6-phenyldodecane.

EXAMPLE 5

(ZSM-38)

A benzene/1-dodecene feed stream (4:1 molar ratio) was brought into contact with zeolite HZSM-38 at 200° C., 215 psig and WHSV of 30 hr$^{-1}$. Ninety-four percent of the dodecene was reacted, with selectivity to phenyldodecane of 73%. Isomeric phenyldodecane distribution was: 37% 2-phenyldodecane, 19% 3-phenyldodecane, 13% 4-phenyldodecane, 14% 5-phenyldodecane and 16% 6-phenyldodecane, with 78% selectivity to the linear phenyldodecane.

EXAMPLE 6

(REY)

REY, a faujasite-type zeolite, was utilized in the flow reactor at 200° C. and 220 psig. A benzene/1-dodecene feed stream (molar ratio 4:1) was passed across the catalyst bed at WHSV of 30 hr$^{-1}$. Product effluent analysis revealed 89% conversion of $C_{12}=$ and 85% selectivity to phenyldodecane. Isomeric phenyldodecane product distribution was: 25% 2-phenyldodecane, 20% 3-phenyldodecane, 18% 4-phenyldodecane, 19% 5-phenyldodecane and 18% 6-phenyldodecane. Ninety-two percent of the phenyldodecane produced was the linear product.

Table I below is a summary of the isomeric distribution of the phenyldodecane product in each of the foregoing examples. As can be seen, the zeolite catalysts of Examples 1 thru 5 had product spectrums having significantly greater proportions of the phenylalkanes having the more external (i.e. relatively lower carbon number) phenyl substitution as compared to the faujasite-type zeolite of Example 6. This is especially striking when comparing the selectivity to the 2-phenyldodecane isomer, as shown in Table II.

TABLE I

| Catalyst Comparison - Phenyldodecane Isomer Distribution | | | | | | |
|---|---|---|---|---|---|---|
| Example | Catalyst | 2-φ | 3-φ | 4-φ | 5-φ | 6-φ | % Linear |
| 1 | HZSM-4 | 57% | 25% | 8% | 5% | 5% | 90% |
| 2 | Beta | 57% | 18% | 10% | 7% | 8% | 53% |
| 3 | HZSM-20 | 51% | 21% | 11% | 9% | 8% | 100% |
| 4 | Linde Type L | 40% | 18% | 16% | 15% | 11% | 88% |
| 5 | HZSM-38 | 37% | 19% | 13% | 14% | 16% | 78% |
| 6 | REY | 25% | 20% | 18% | 19% | 18% | 92% |

TABLE II

| Example | Catalyst | Selectivity* to 2-φ-$C_{12}$ |
|---|---|---|
| 1 | HZSM-4 | 57% |
| 2 | Beta | 57% |
| 3 | HZSM-20 | 51% |
| 4 | Linde Type L | 40% |
| 5 | HZSM-38 | 37% |
| 6 | REY | 25% |

*Defined as % 2-φ-$C_{12}$ in total linear φ-$C_{12}$.

The unusual product spectrum demonstrated above would be of great value in many useful applications. For example, it is well known in the detergent field that the biodegradability of alkylbenzenesulfonic acid based detergents is enhanced when the average substituent position of the benzene ring on the alkyl chain is reduced—e.g. a detergent based on (2-alkyl)benzenesulfonic acid is more easily biodegraded than is one based on (3-alkyl)benzenesulfonic acid, which in turn is more biodegradable than another detergent based on (4-alkyl)benzenesulfonic acid, and so forth. Since sulfonation of a phenylalkane mixture to produce alkylbenzenesulfonic acids would not significantly alter the original isomer distribution, it will be readily apparent that phenylalkanes produced as disclosed herein could ultimately be utilized to produce detergents which have improved biodegradability as compared to those heretofore available.

Having thus described the present invention with the aid of certain specific examples thereof, it is to be understood that such examples are intended to be merely illustrative of the disclosed process. Many variations thereon may be made without departing from the spirit of the disclosed invention, as will be evident to those skilled in the art, and such variations are intended to come within the scope of the following claims:

What is claimed is:

1. A process for the selective alkylation of aromatic compounds with relatively long chain length alkylating agents to selectively produce 2-phenylalkanes; said alkylating agents comprising aliphatic or aromatic organic compounds having one or more available reactive alkyl groups of at least five carbons in the hydrocarbon chain; said process comprising contacting said aromatic compound with said alkylating agent in the presence of a crystalline zeolite catalyst, at a temperature of between about 50° C. and about 500° C. and a pressure withn the approximate range of $2.5 \times 10^4$ N/m$^2$ to $2.5 \times 10^7$ N/m$^2$; said crystalline zeolite catalyst being chosen from the group consisting of: mazzite, zeolite Beta, ZSM-20, ZSM-38 and synthetic and naturally occurring isotypes thereof.

2. A process as described in claim 1 wherein said alkyl groups have between six and twenty carbon atoms in the linear hydrocarbon chain.

3. A process as described in claim 1 wherein said aromatic compound is benzene.

4. A process as described in claim 1 wherein said aromatic compound comprises a benzene ring having from one to two substituents thereon.

5. A process as described in claim 1 wherein said temperature is within the approximate range of from 100° C. to 350° C. and said pressure is between about $10^5$ N/m² and about $5 \times 10^6$ N/m².

6. A process as described in claim 1 wherein said zeolite has the crystal structure of mazzite.

7. A process as described in claim 1 wherein said zeolite has the crystal structure of zeolite Beta.

8. A process as described in claim 1 wherein said zeolite has the crystal structure of ZSM-20.

9. A process as described in claim 1 wherein said zeolite has the crystal structure of ZSM-38.

10. A process as described in claim 1 wherein said zeolite is steamed prior to use.

11. A process as described in claim 1, 6, 7, 8, 9 or 10 wherein said zeolite is combined with a binder therefor.

* * * * *